(12) United States Patent
Santangelo et al.

(10) Patent No.: US 11,253,248 B2
(45) Date of Patent: Feb. 22, 2022

(54) ARTICULATED MENISCAL REPAIR INSTRUMENT

(71) Applicant: Smith & Nephew, Inc., Memphis, TN (US)

(72) Inventors: Stephen Santangelo, Memphis, TN (US); Anthony O'Leary, Memphis, TN (US); Matthew Dennis Cunningham, Memphis, TN (US)

(73) Assignee: SMITH & NEPHEW, INC., Memphis, TN (US)

( * ) Notice: Subject to any disclaimer, the term of this patent is extended or adjusted under 35 U.S.C. 154(b) by 258 days.

(21) Appl. No.: 16/328,851

(22) PCT Filed: Aug. 29, 2017

(86) PCT No.: PCT/US2017/049131
§ 371 (c)(1),
(2) Date: Feb. 27, 2019

(87) PCT Pub. No.: WO2018/044898
PCT Pub. Date: Mar. 8, 2018

(65) Prior Publication Data
US 2019/0183482 A1 Jun. 20, 2019

Related U.S. Application Data

(60) Provisional application No. 62/381,921, filed on Aug. 31, 2016.

(51) Int. Cl.
*A61B 17/04* (2006.01)
*A61B 17/00* (2006.01)

(52) U.S. Cl.
CPC ...... *A61B 17/0401* (2013.01); *A61B 2017/00309* (2013.01); *A61B 2017/00314* (2013.01);
(Continued)

(58) Field of Classification Search
CPC ...... A61B 17/0401; A61B 2017/00327; A61B 2017/00743; A61B 2017/00314;
(Continued)

(56) References Cited

U.S. PATENT DOCUMENTS 3,470,876 A * 10/1969 Barchilon ............ A61B 1/0052
604/95.04
4,996,974 A * 3/1991 Ciarlei ................. A61B 1/0052
138/120

(Continued)

FOREIGN PATENT DOCUMENTS

EP 2907466 A1 8/2015
WO 2015/193881 A1 12/2015

OTHER PUBLICATIONS

International Search Report and Written Opinion from related PCT Application No. PCT/US2017/049131 dated Oct. 11, 2017.
(Continued)

*Primary Examiner* — Julian W Woo
(74) *Attorney, Agent, or Firm* — Burns & Levinson, LLP; Joseph M. Maraia

(57) ABSTRACT

A meniscal repair instrument includes an articulating mechanism configured to move a needle on the tip in a controlled arc. Multiple directions of motion are provided in order to facilitate the deployment of suture anchors. In one aspect, the articulating mechanism includes a series of movable members that are coupled together by two wires that are provided with a push/pull force via a control mechanism.

17 Claims, 19 Drawing Sheets

(52) U.S. Cl.
CPC .............. *A61B 2017/00327* (2013.01); *A61B 2017/00367* (2013.01); *A61B 2017/00743* (2013.01); *A61B 2017/0409* (2013.01); *A61B 2017/0417* (2013.01); *A61B 2017/0464* (2013.01)

(58) Field of Classification Search
CPC .. A61B 2017/0417; A61B 2017/00309; A61B 2017/00367; A61B 2017/0464; A61B 2017/0409
See application file for complete search history.

(56) References Cited

U.S. PATENT DOCUMENTS

| | | | | | |
|---|---|---|---|---|---|
| 5,167,221 | A | * | 12/1992 | Chikama | A61B 1/0052 600/149 |
| 5,328,467 | A | * | 7/1994 | Edwards | A61M 25/0138 600/373 |
| 5,383,852 | A | * | 1/1995 | Stevens-Wright | A61M 25/0136 604/95.04 |
| 5,676,653 | A | * | 10/1997 | Taylor | A61M 25/0144 604/523 |
| 5,916,146 | A | * | 6/1999 | Allotta | A61B 1/0051 600/141 |
| 7,331,958 | B2 | * | 2/2008 | Falwell | A61B 18/1492 604/95.04 |
| 8,298,177 | B2 | * | 10/2012 | Selkee | A61M 25/0136 604/95.01 |
| 8,790,243 | B2 | * | 7/2014 | Cooper | A61B 17/062 600/101 |
| 8,827,897 | B2 | * | 9/2014 | Sato | G02B 23/2476 600/146 |
| 8,911,428 | B2 | * | 12/2014 | Cooper | A61B 34/30 606/1 |
| 9,717,517 | B2 | * | 8/2017 | Stroup | A61B 17/29 |
| 9,795,375 | B2 | * | 10/2017 | Lore | A61B 17/0401 |
| 9,808,597 | B2 | * | 11/2017 | Vargas | A61M 25/0138 |
| 10,136,908 | B2 | * | 11/2018 | Mueller | A61B 17/2833 |
| 10,172,636 | B2 | * | 1/2019 | Stulen | A61B 17/320068 |
| 11,191,424 | B2 | * | 12/2021 | Boulais | A61B 1/00071 |
| 2007/0038230 | A1 | | 2/2007 | Stone et al. | |
| 2007/0225562 | A1 | | 9/2007 | Spivey et al. | |
| 2015/0080924 | A1 | | 3/2015 | Stulen et al. | |

OTHER PUBLICATIONS

Chinese Application No. 201780050656.6 Text of First Office Action, dated Aug. 29, 2017.
Chinese Application No. 201780050656.6 Search Report, dated Aug. 29, 2017.

* cited by examiner

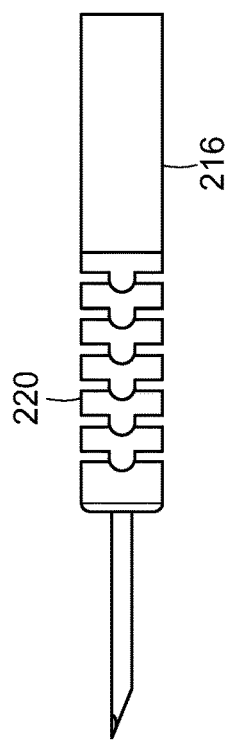
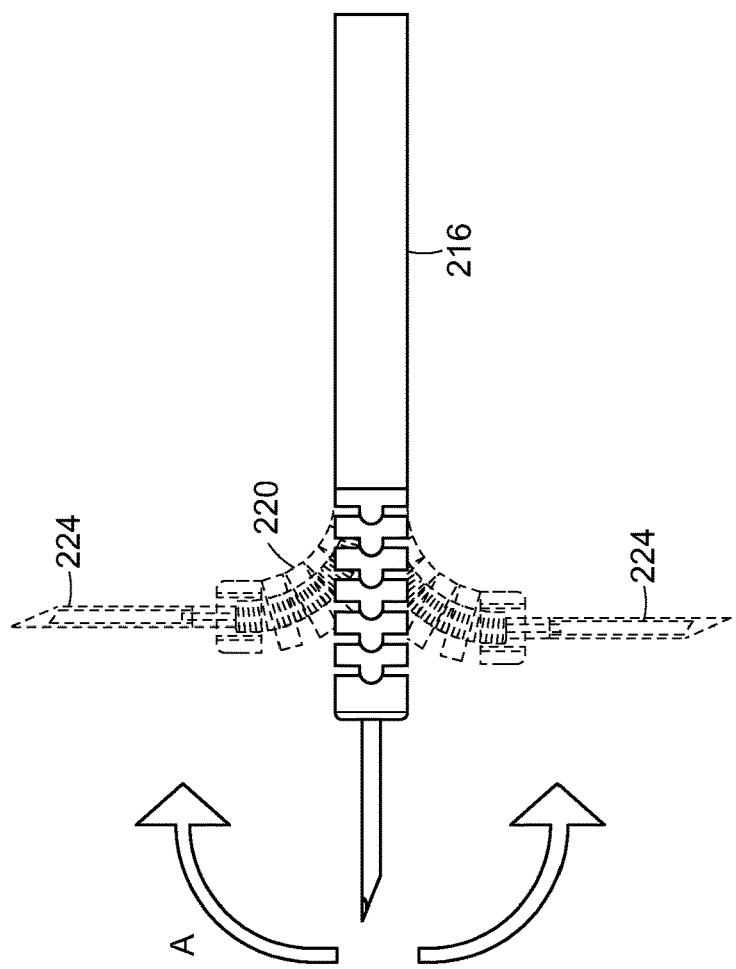
FIG. 3-1
FIG. 3-2

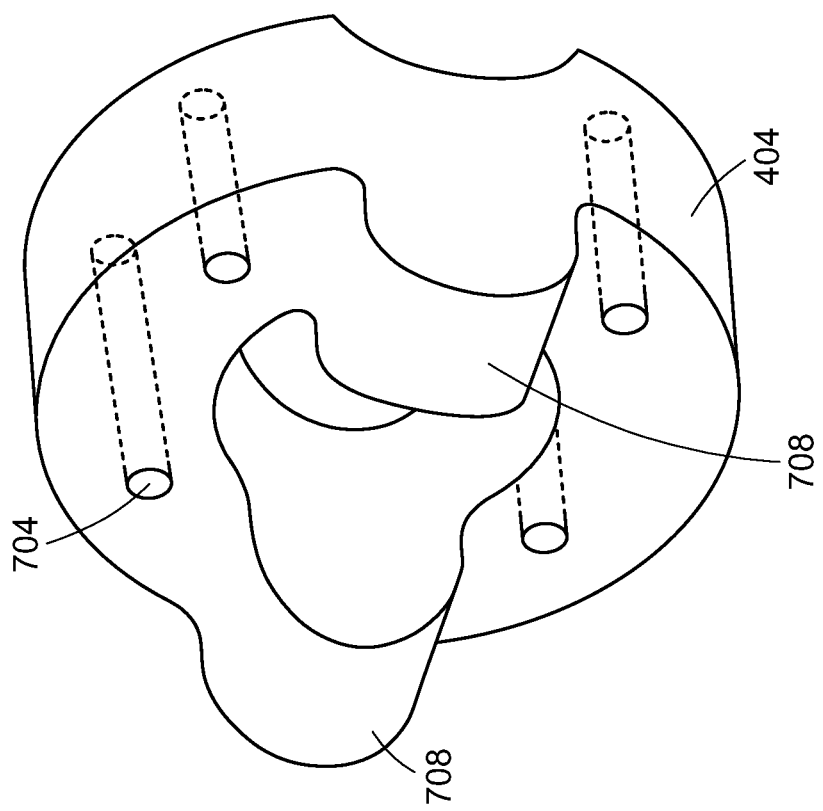
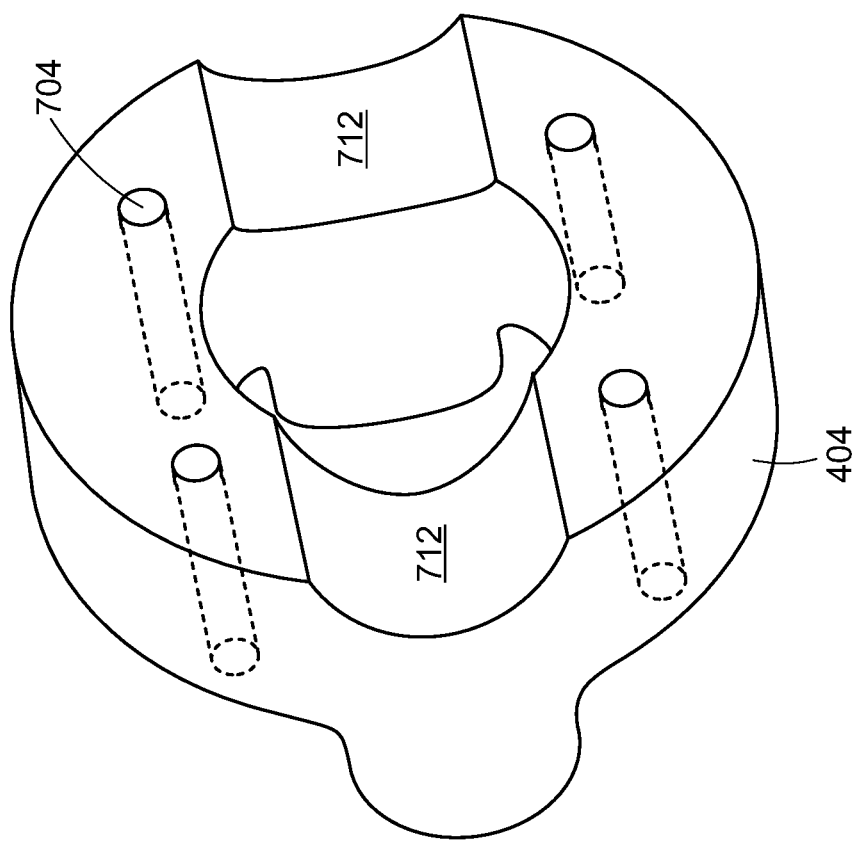
FIG. 7

ARTICULATED MENISCAL REPAIR INSTRUMENT

CROSS-REFERENCE TO RELATED APPLICATIONS

This application is the U.S. national phase entry under 35 U.S.C. § 371 of International Application No. PCT/US2017/049131, filed Aug. 29, 2017, entitled "Articulated Meniscal Repair Instrument," which in turn claims priority to and benefit of U.S. Provisional Application No. 62/381,921, filed Aug. 31, 2016, the entire contents of which are herein incorporated by reference for all purposes.

BACKGROUND

In order to reach a damaged meniscus in the knee, existing state of the art meniscal repair devices utilize fixed, that is, rigid, needle tips with, for example, straight or curved profiles. Due to the juxtaposition of components within the knee anatomy, however, these fixed dimension repair devices cannot readily access meniscal tears located throughout all regions of the meniscus.

What is needed is a repair device that is able to access all regions of the meniscus to facilitate repairs.

BRIEF SUMMARY OF THE INVENTION

In one aspect, a meniscal repair instrument comprises a flexible shaft; an articulating mechanism, disposed about the flexible shaft; and a control mechanism, coupled to the articulating mechanism, configured to move the articulating mechanism through a controlled arc of motion.

The articulating mechanism may comprise a plurality of movable members disposed about the flexible shaft and coupled in series to one another.

The articulating mechanism may comprise an articulated tube disposed about the flexible shaft and include two flexible bands running in parallel to one another through the articulated tube.

BRIEF DESCRIPTION OF THE DRAWINGS

Various aspects of at least one embodiment of the present disclosure are discussed below with reference to the accompanying figures. It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. For purposes of clarity, not every component may be labeled in every drawing. The figures are provided for the purposes of illustration and explanation and are not intended as a definition of the limits of the invention. In the figures:

FIGS. 2-1 and 2-2 present perspective views of a meniscal repair device in accordance with an aspect of the present disclosure;

FIGS. 3-1 and 3-2 are each a close-up of the circled portion shown in FIGS. 2-1 and 2-2;

FIGS. 4-1 and 4-2 present a flexible portion of the meniscal device in accordance with an embodiment of the present disclosure;

FIG. 7 presents the links of the flexible portion shown in FIGS. 4-1 and 4-2;

FIGS. 11-1 and 11-2 are perspective views of a thumbwheel portion of the control mechanism of FIG. 8;

FIGS. 14-1-14-3 are exploded views of the flexible portion shown in FIG. 13.

DETAILED DESCRIPTION

Figures 1, 1A:
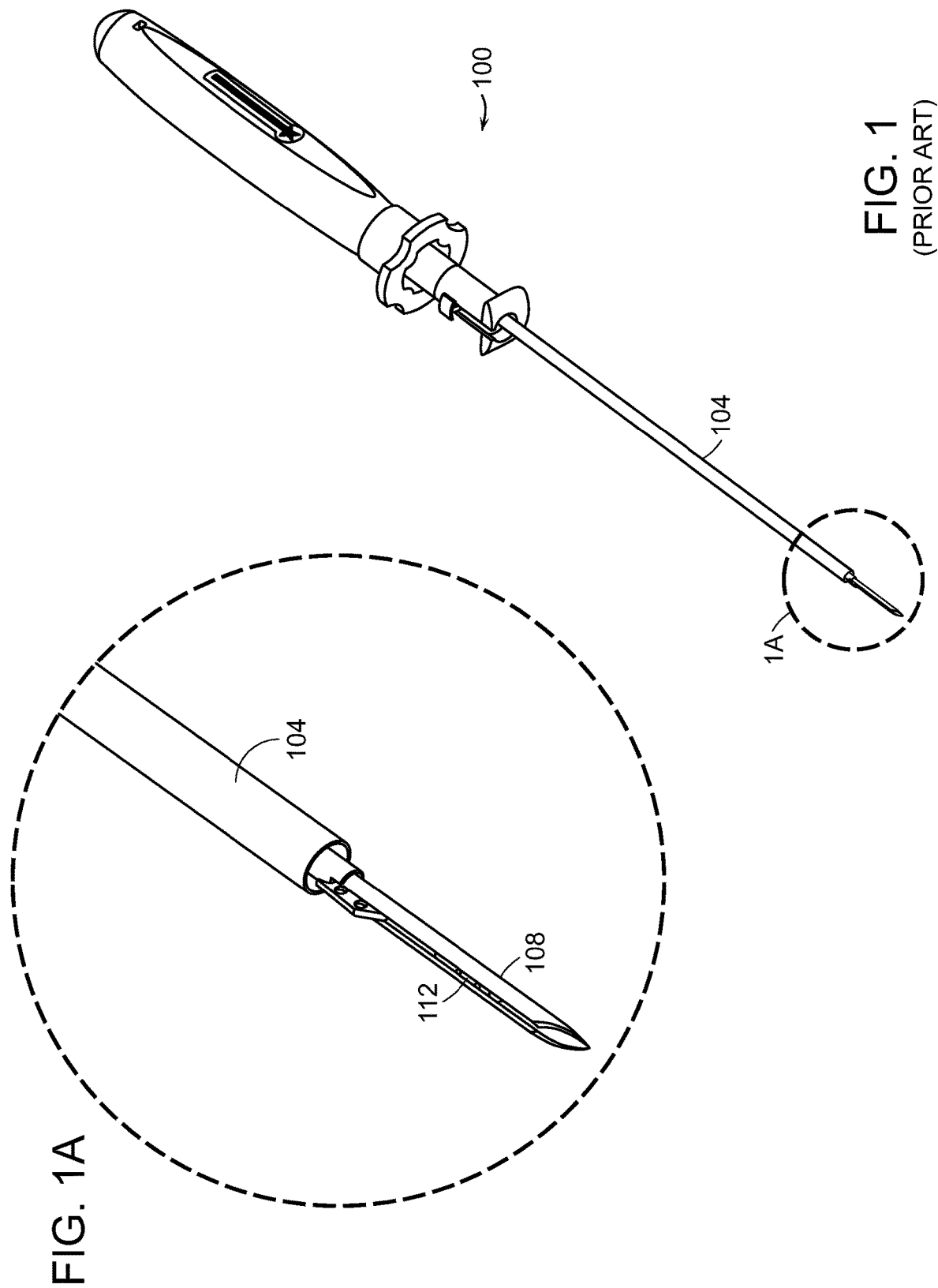
FIGS. 1 and 1A present a known meniscal repair device.

In the following detailed description, numerous specific details are set forth in order to provide a thorough understanding of the aspects of the present disclosure. It will be understood by those of ordinary skill in the art that these may be practiced without independently some of these specific details. In other instances, well-known methods, procedures, components and structures may not have been described in detail so as not to obscure the embodiments.

Prior to explaining at least one aspect of the present disclosure in detail, it is to be understood that it is not limited in its application to the details of construction and the arrangement of the components set forth in the following description or illustrated in the drawings. There are various ways of being practiced or carried out. Also, it is to be understood that the phraseology and terminology employed herein are for the purpose of description only and should not be regarded as limiting.

It is appreciated that certain features, are, for clarity, described in the context of separate embodiments but may also be provided in combination in a single embodiment. Conversely, various features are, for brevity, described in the context of a single embodiment but may also be provided separately or in any suitable sub-combination.

In the broadest sense, aspects of the present disclosure are directed to an articulating mechanism configured to move a needle on the tip of a meniscal repair instrument in a controlled arc. Multiple directions of motion are provided in order to facilitate the deployment of suture anchors. In one aspect, the articulating mechanism includes a series of movable members that are coupled together by two wires that are provided with a push/pull force via a control mechanism. This configuration allows these movable members to move relative to each other, as will be explained in more detail below.

Referring now to FIGS. 1 and 1A, a known meniscal repair device 100 utilizes a straight distal portion 104. A rigid needle tip 108 is located at the end of the distal portion 104 to provide the repair devices 112. These rigid devices 100 often cannot readily reach all areas of the meniscus and, therefore, are inadequate in some situations.

Figures 1, 2:
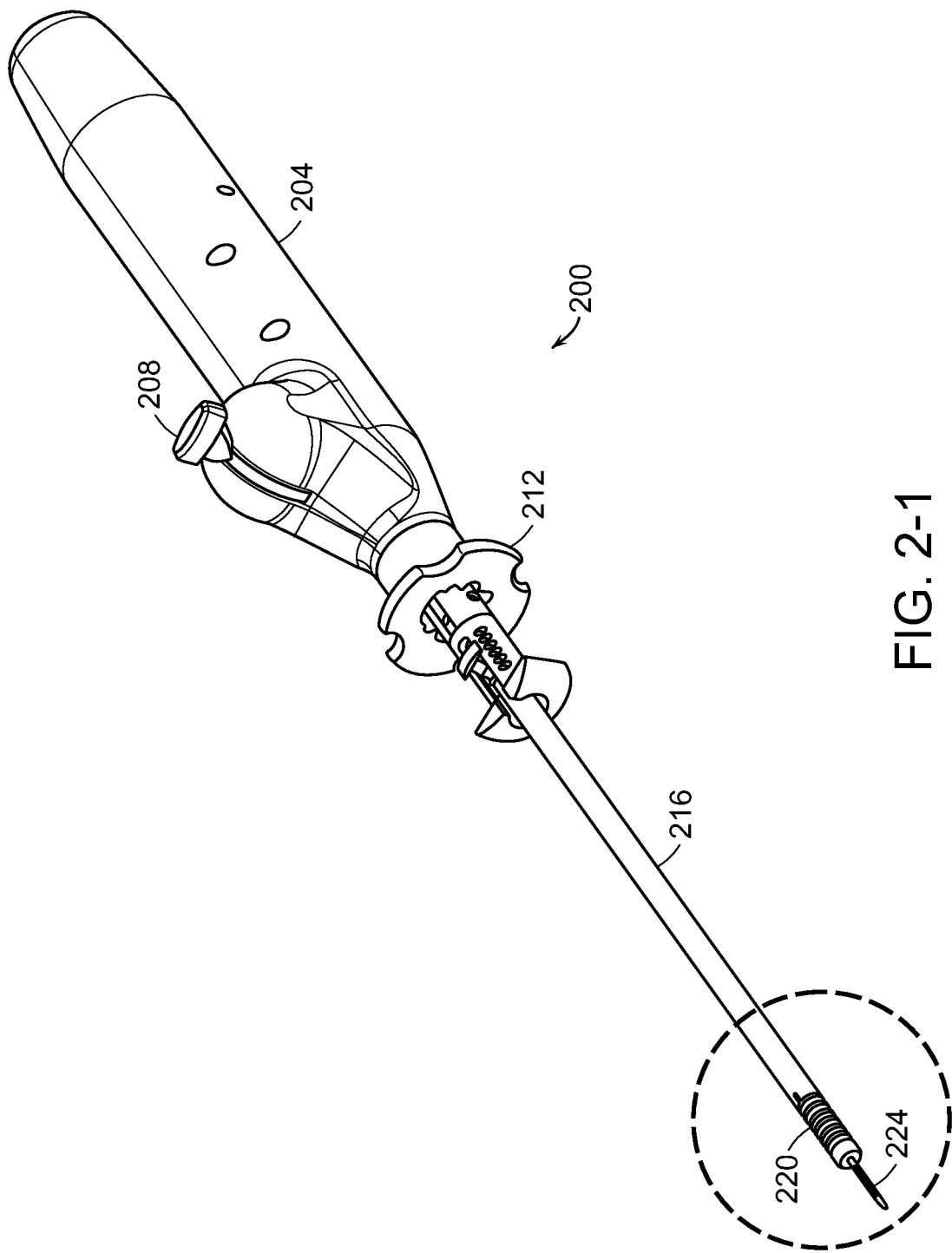
Figure 2:
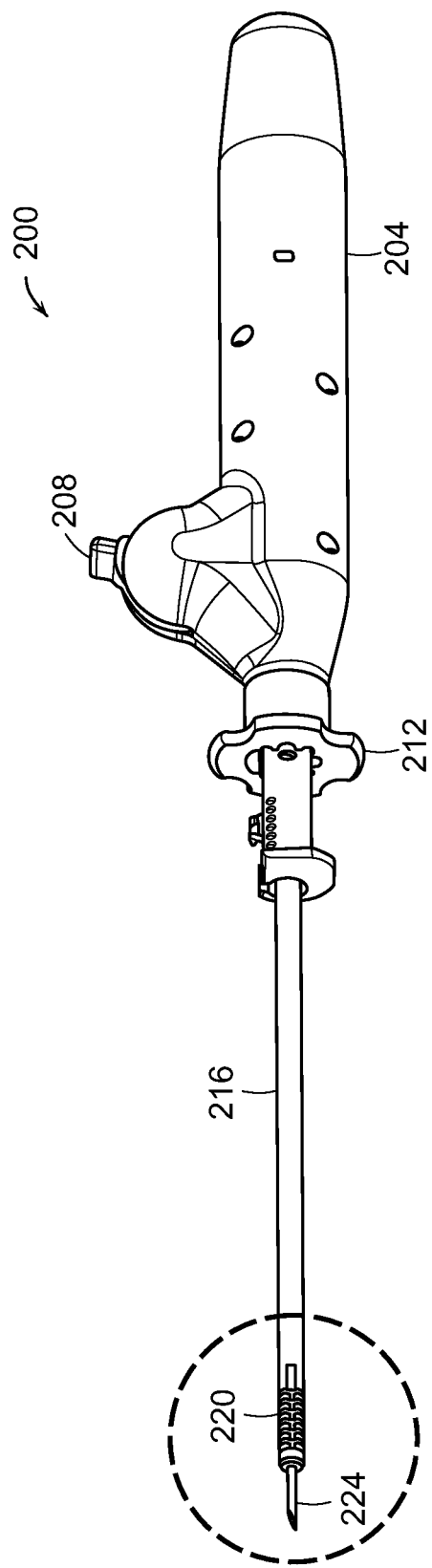

In accordance with one aspect of the present disclosure, a meniscal repair device 200 as shown in FIGS. 2-1 and 2-2, includes a handle 204, a control mechanism 208 coupled to the handle 204, a flexible actuator pushrod 212, also coupled to the handle 204, and a support tube 216. The support tube 216 includes a flexible portion 220 and a needle tip 224 at a distal end of the support tube 216.

Figures 1, 14:
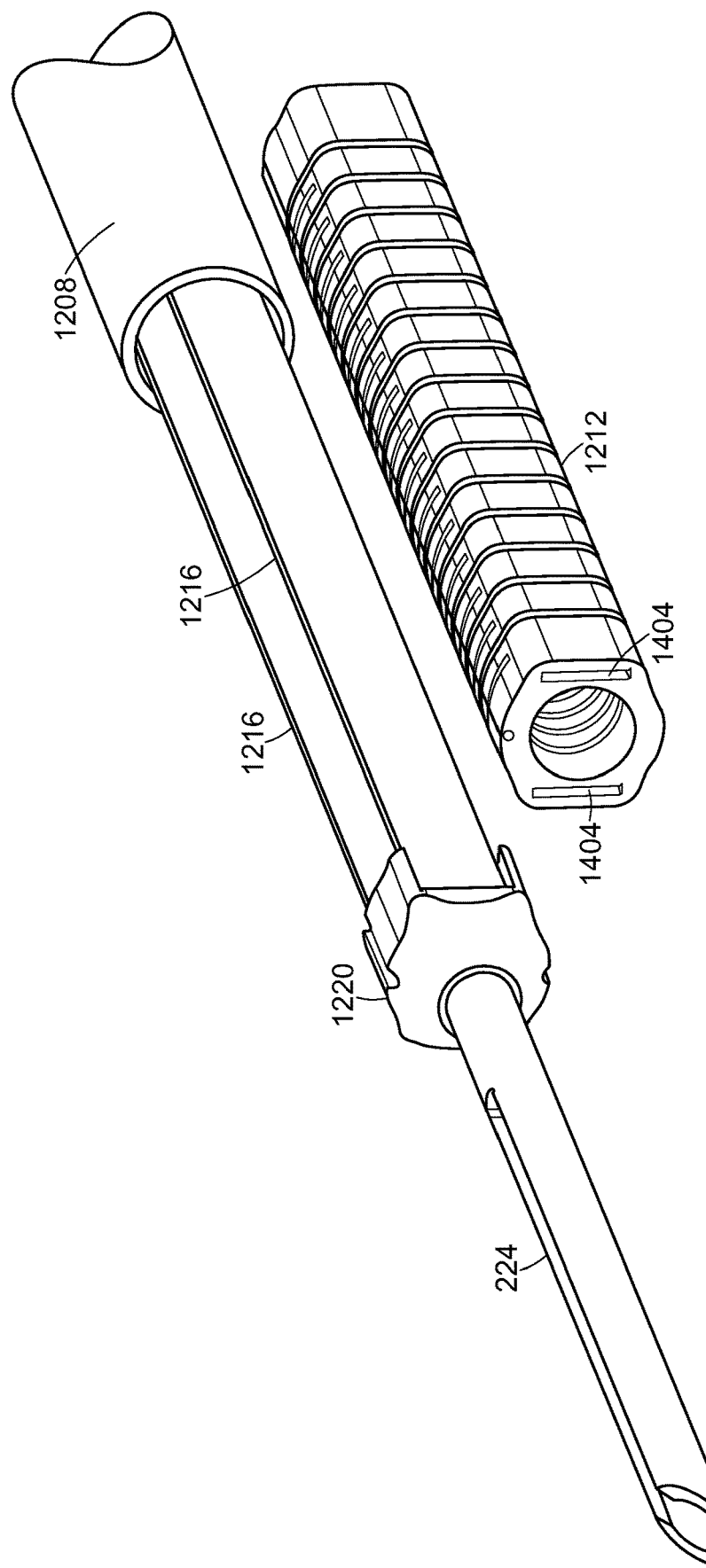
Figures 2, 14:
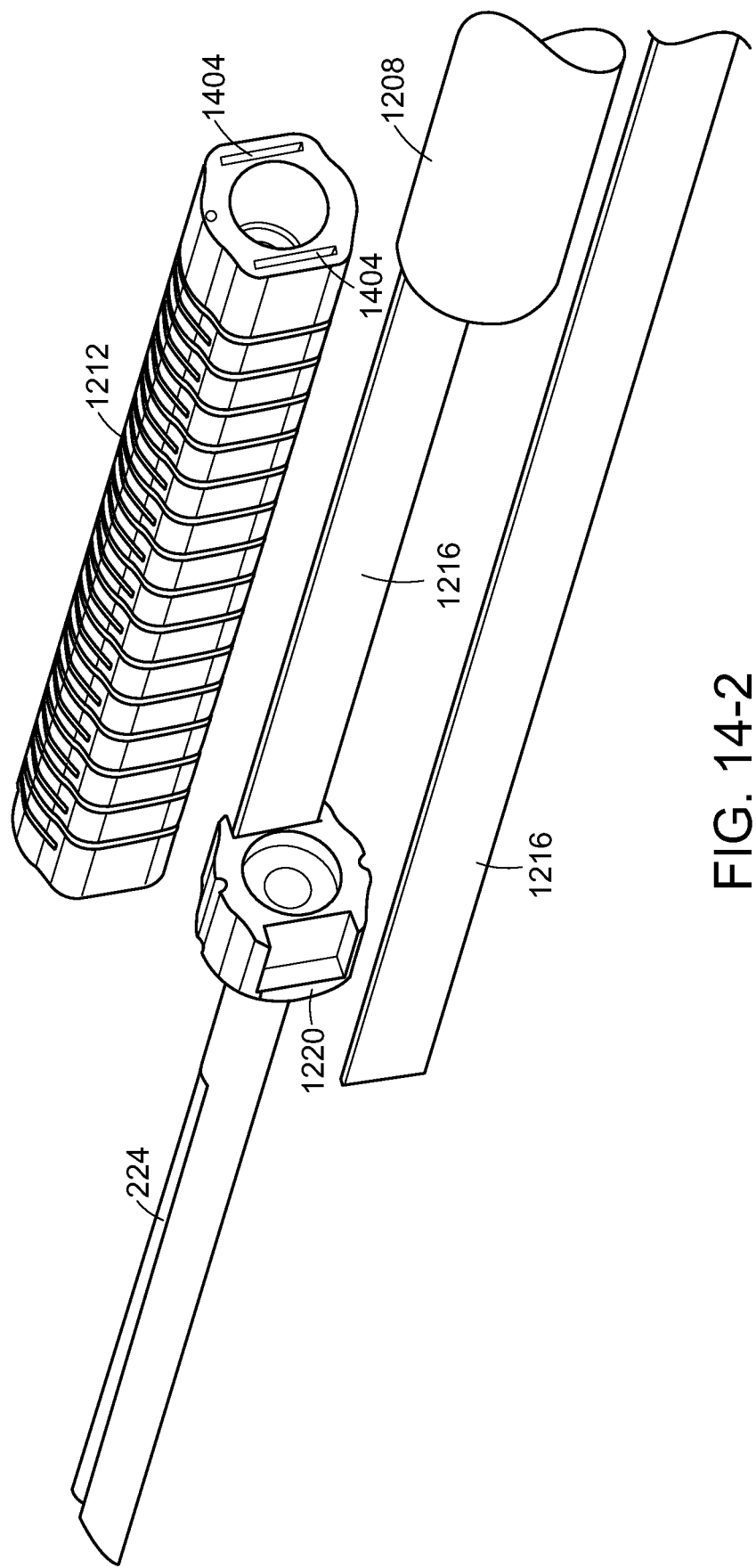
Figures 3, 14:
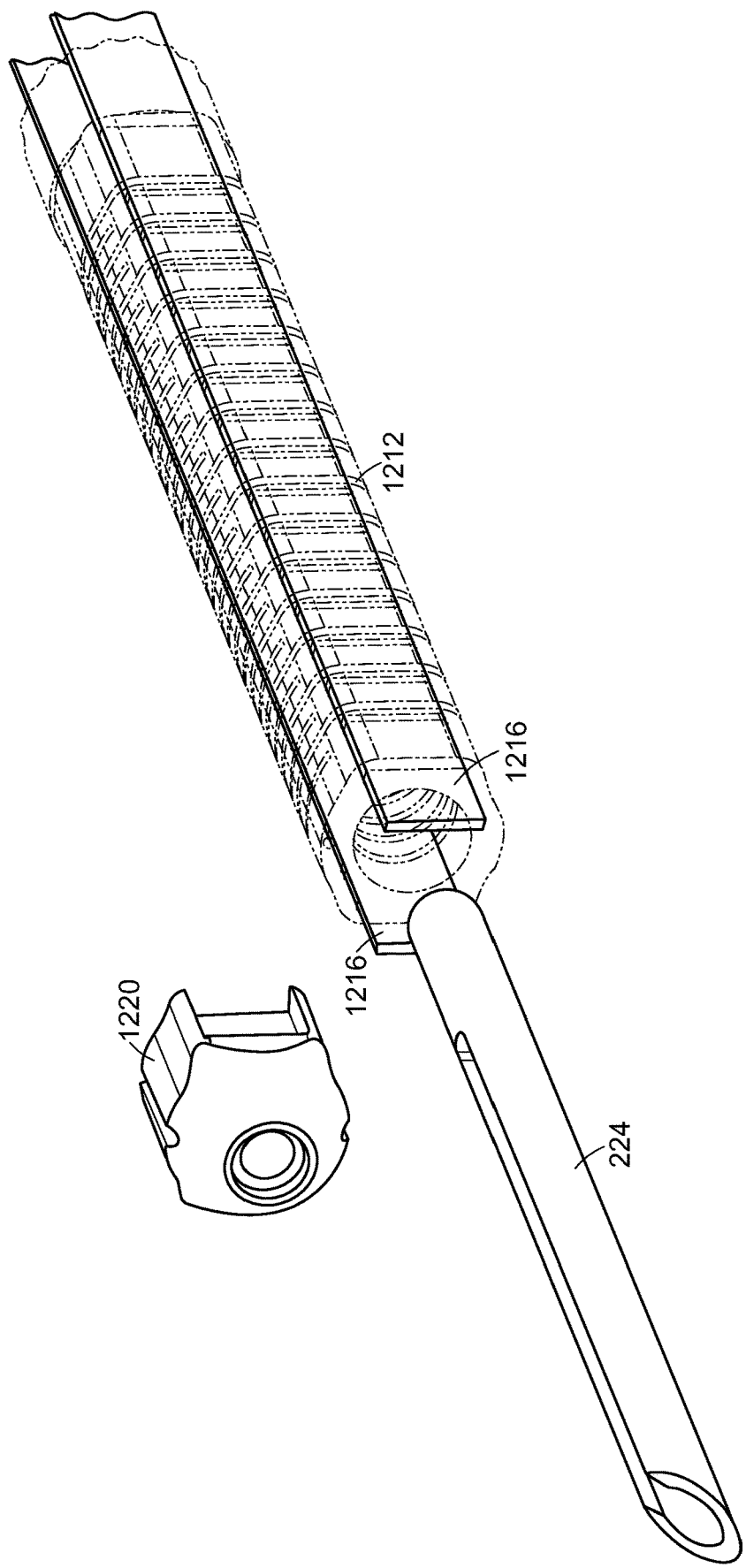

As shown in FIGS. 3-1 and 3-2, each a close-up of the circled portion shown in FIGS. 2-1 and 2-2, the flexible portion 220 is able to flex in an arc A defined about the support tube 216. As will be described in more detail below, the flexible portion 220 includes a number of components and control wires that are coupled to the control mechanism 208 in order to facilitate the amount of flexure of the distal end of the device 200.

Figures 1, 4:
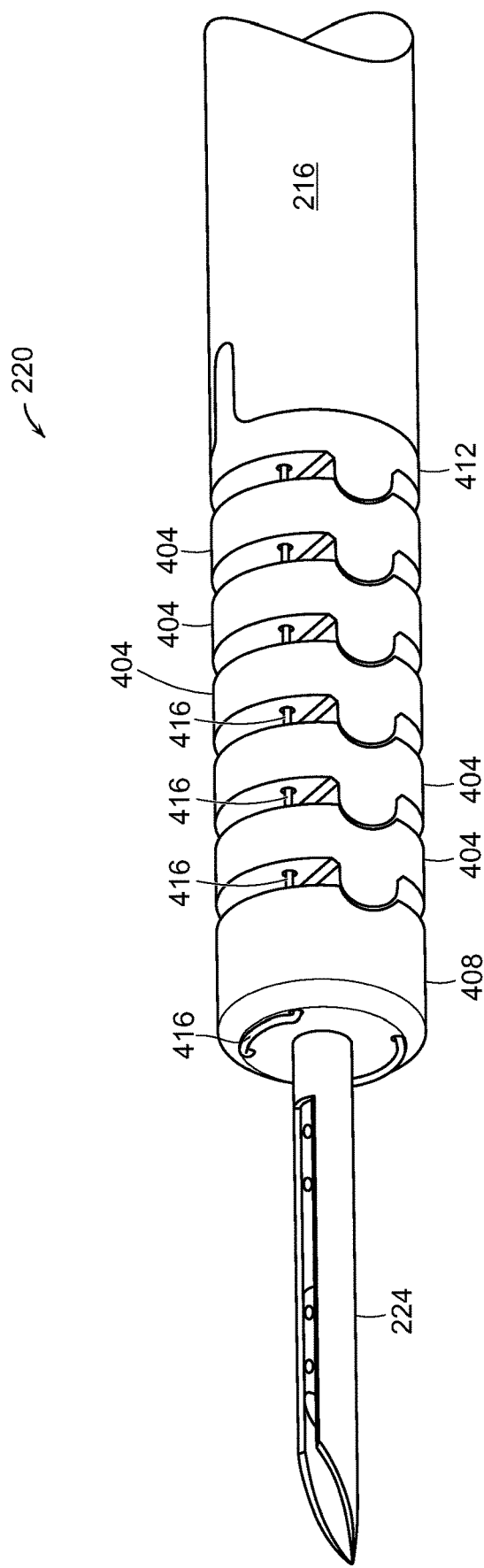
Figures 2, 4:
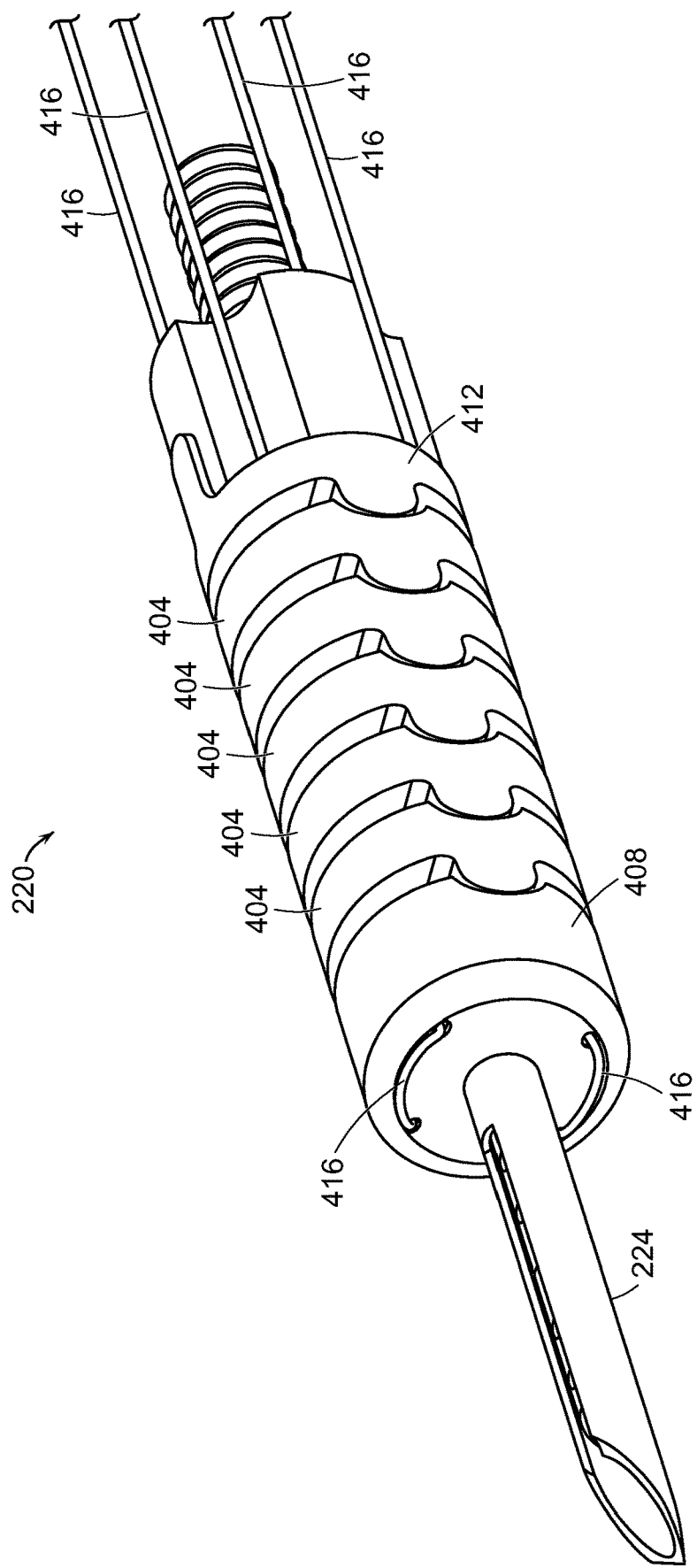

The flexible portion 220 includes a number of interconnected links 404 that are disposed between a lead link 408 and an end link 412, as shown in FIGS. 4-1 and 4-2. The end link 412 is coupled to the support tube 216 while the lead link 408 is coupled to the needle tip 224. Two wires 416 are threaded through the lead link 408, the end link 412 and the intervening links 404 and are used to control the direction and amount of bend of the flexible portion.

Figure 5:
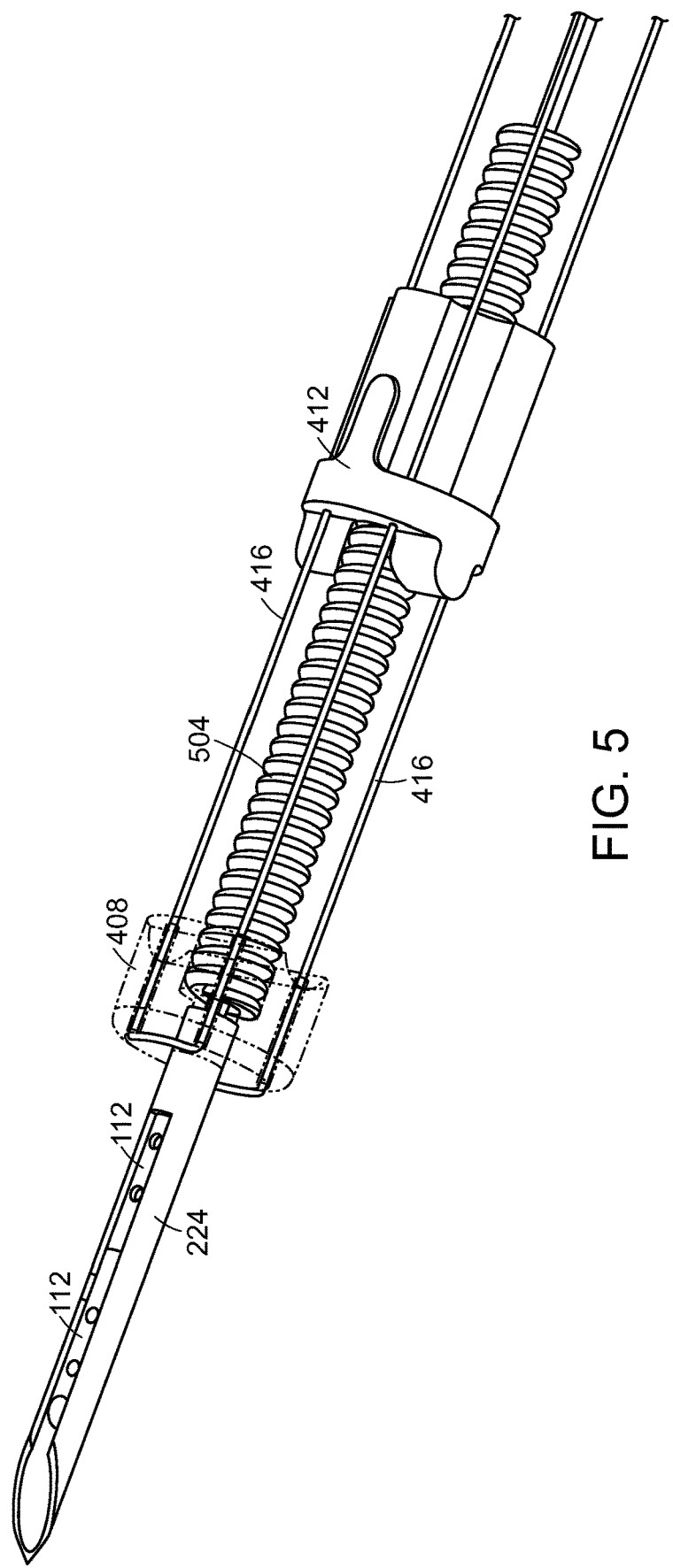
FIG. 5 is a cutaway view of the flexible portion shown in FIGS. 4-1 and 4-2.

As shown in FIG. 5, a flexible shaft 504 runs through the links 404 and into the support tube 216. This flexible shaft 504 also bends as the flexible portion 220 is bent. In addition, the meniscal implants are shown as being disposed in the needle tip 224 prior to insertion for repair of the meniscus. The sutures that are usually attached to a meniscal implants device, however, are not shown for clarity.

Figure 6:
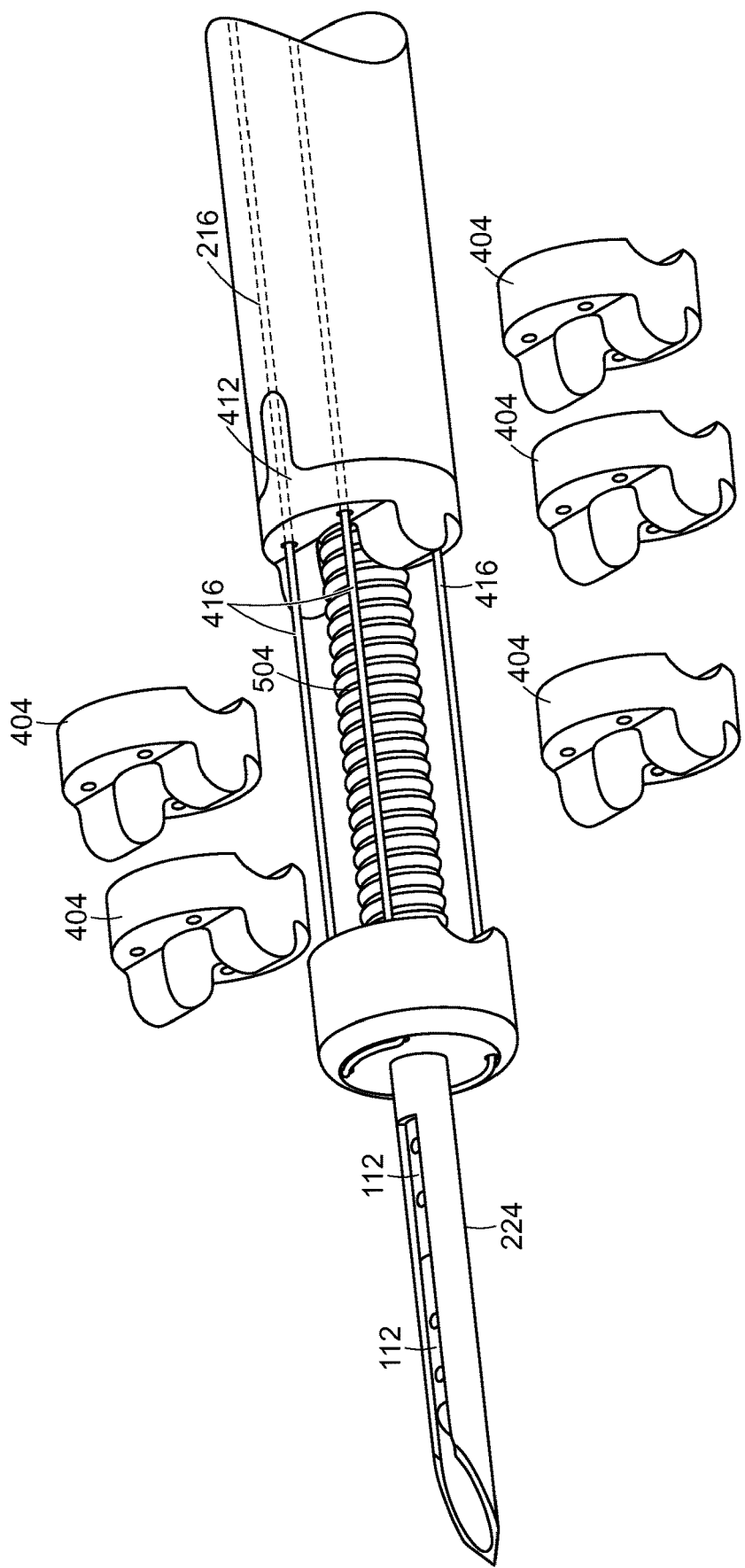
FIG. 6 is an exploded view of the flexible portion shown in FIGS. 4-1 and 4-2.

As shown in FIG. 6, an exploded view of the distal portion of the present device, there are two pairs of wires 416 that traverse the length of the support tube 216 and loop back through the lead link 408 to the control mechanism 208. The two wires 416 operate in a push/pull relationship, per the operation of the control mechanism 208, in order to direct the needle tip 224 and, therefore, the placement of the repair devices 112. The number of intermediate links 404 may be chosen to provide for a different amount of flexure or desired radius.

Each intermediate link 404, as shown in FIG. 7, includes a plurality of wire conduits 704 for the wires 416 to pass through in addition to link projections 708 on one surface and link receptors 712 on the opposite surface. The link projections 708 of one link 404 are meant to couple with the corresponding link receptors 712 of an adjacent link 404 as shown in the figures. The lead link 408 incorporates link receptors 712 but has no need for link projections 708 and, correspondingly, the end link 412 includes link projections 712 but has no need for link receptors 708.

Figure 8:
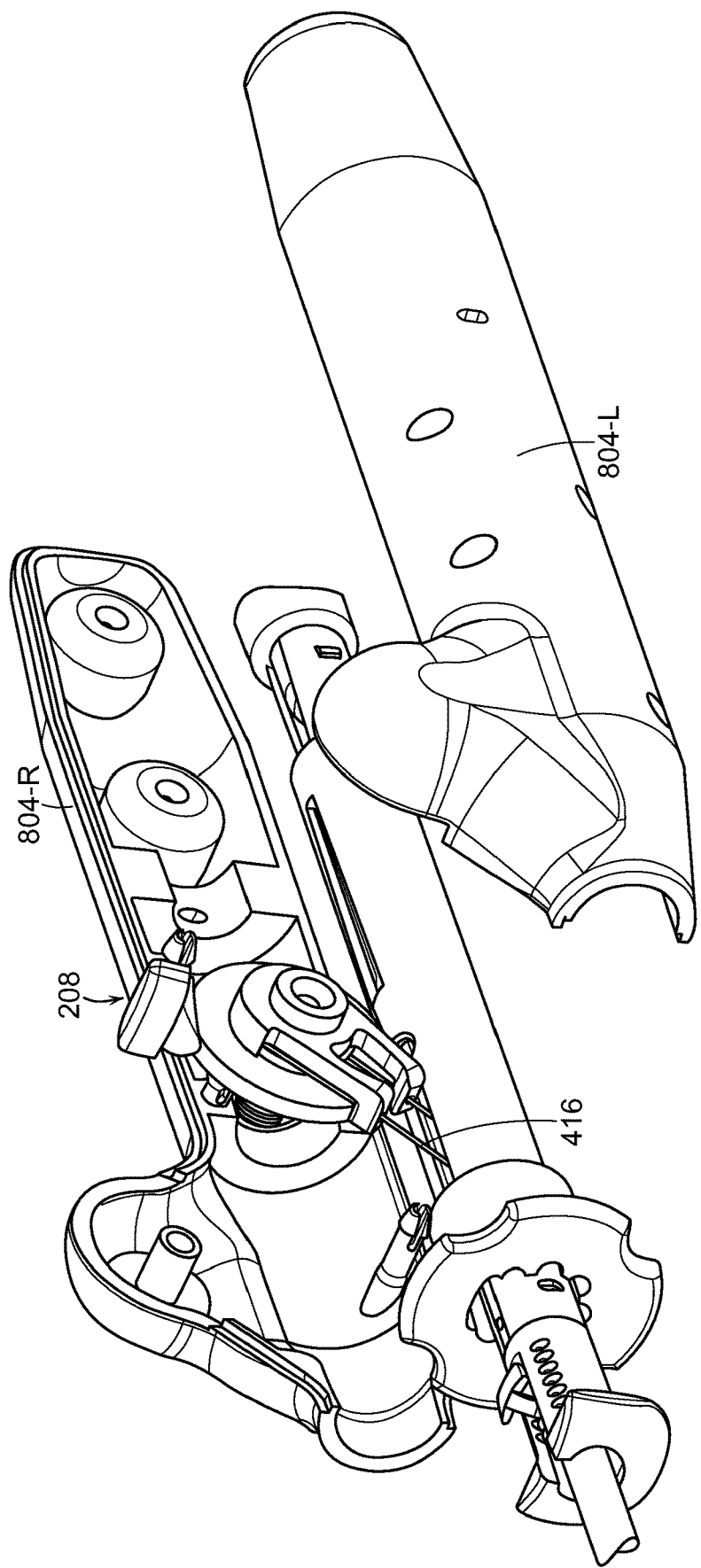
FIG. 8 is an exploded view of a control mechanism in accordance with an aspect of the present disclosure.
Figure 9:
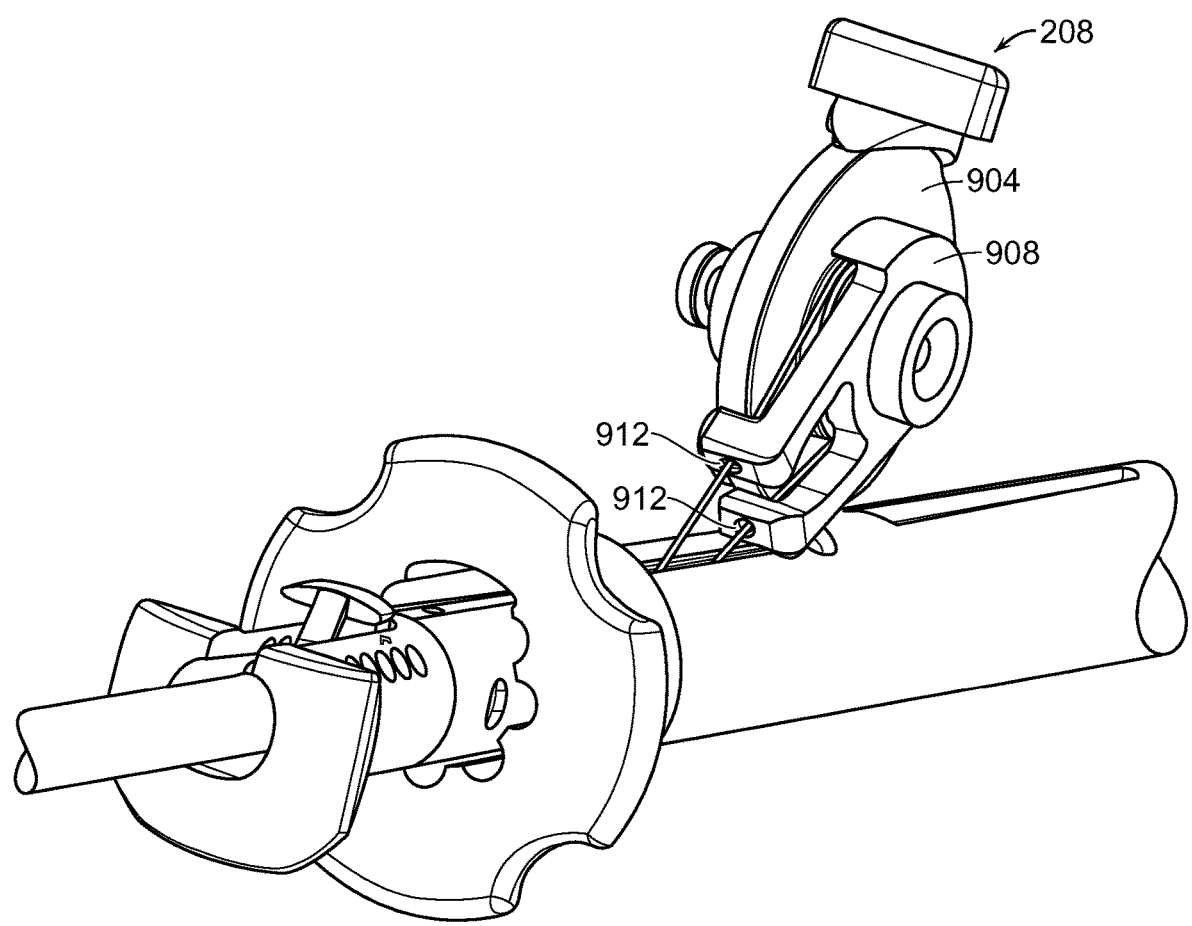
FIG. 9 is a close-up view of the control mechanism of FIG. 8.
Figure 10:
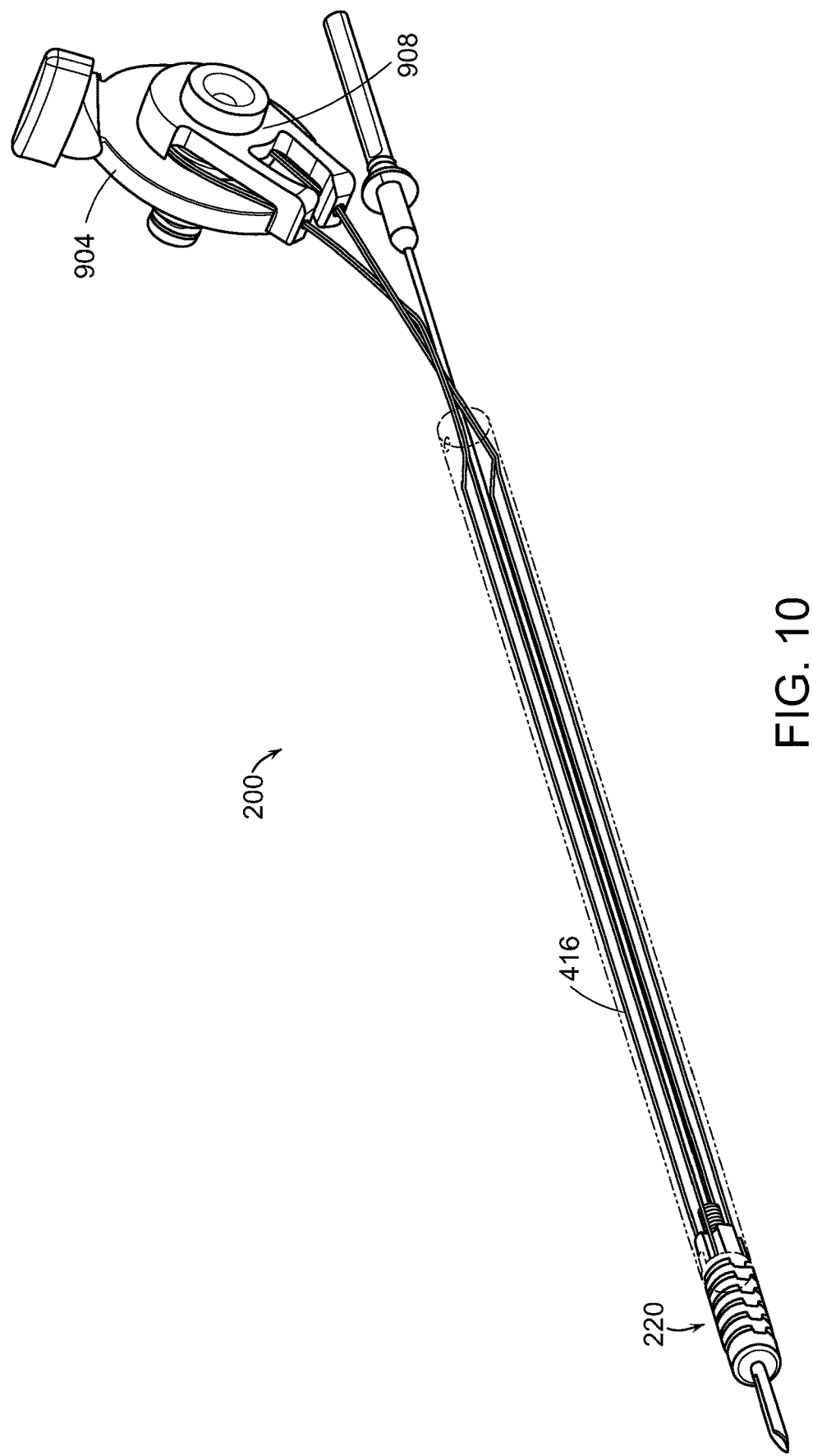
FIG. 10 is a cut-away view of the control mechanism of FIG. 8 in the repair device.

Referring now to FIG. 8, the control mechanism 208 is coupled to the wires 416 that are used to control the flexible portion 220 of the device 200. The control mechanism 208 is mounted between right and left halves 804-R, 804-L of the handle portion 204 and, as shown in FIG. 9, includes a thumbwheel 904 and a wire cradle 908. The wire cradle 908 includes a plurality of openings 912 through which the wires 416 pass in order to provide the push and pull force on the wires 416 necessary to move the flexible portion 220 of the device 200. Advantageously, the direction in which the thumbwheel 904 can be operated defines the plane in which the flexible portion 220 can be maneuvered. In this way, the operator of the device 200 has a visual and tactile mechanism to discern the plane in which the needle tip 224 of the device 200 is operating, as can be seen from FIG. 10. In addition, the control mechanism may include a lock mechanism to hold the distal tip at a specific angle. The lock mechanism could be a friction lock, a ratcheting lock, pawl lock or other approach.

Figures 1, 11:
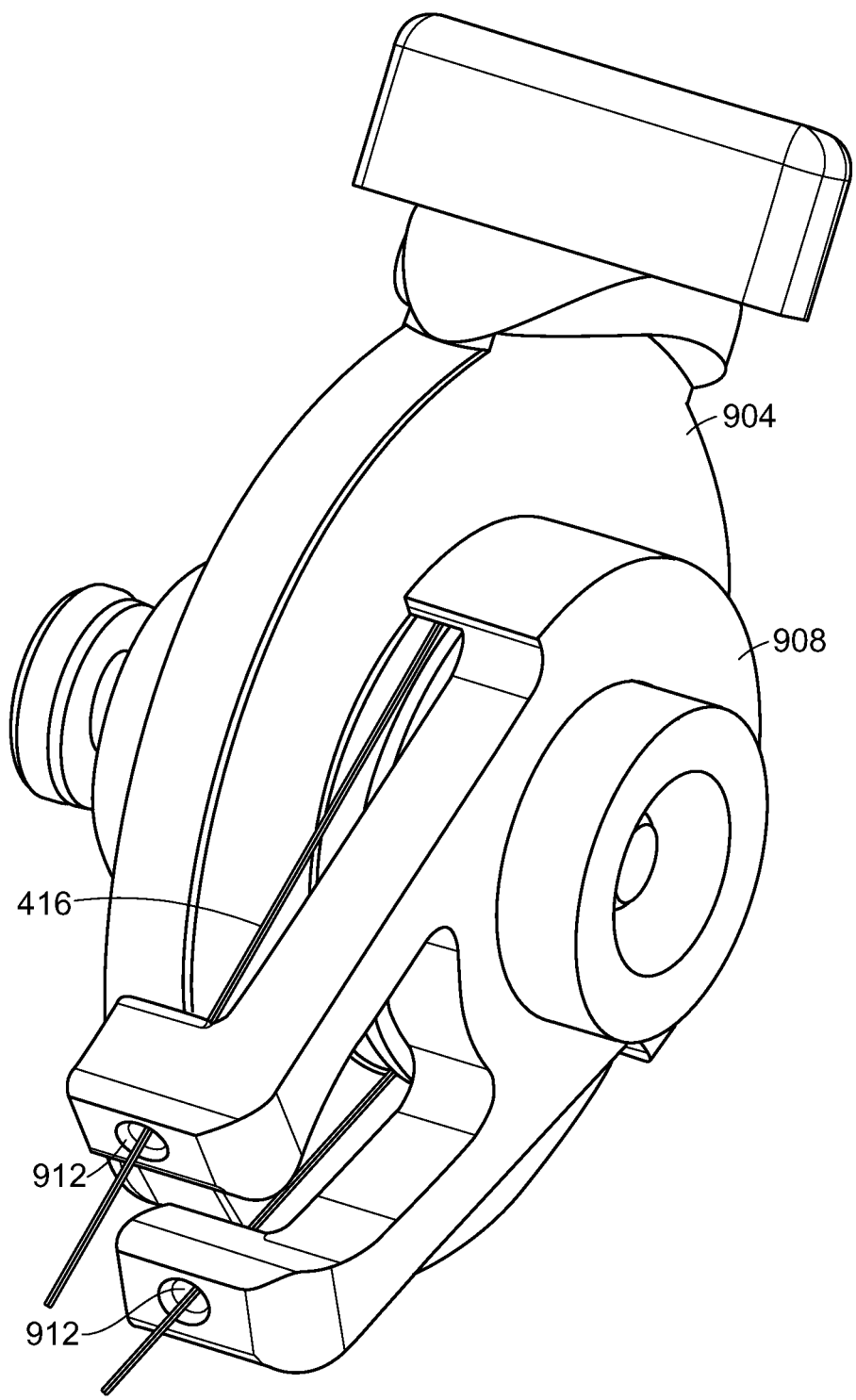
Figures 2, 11:
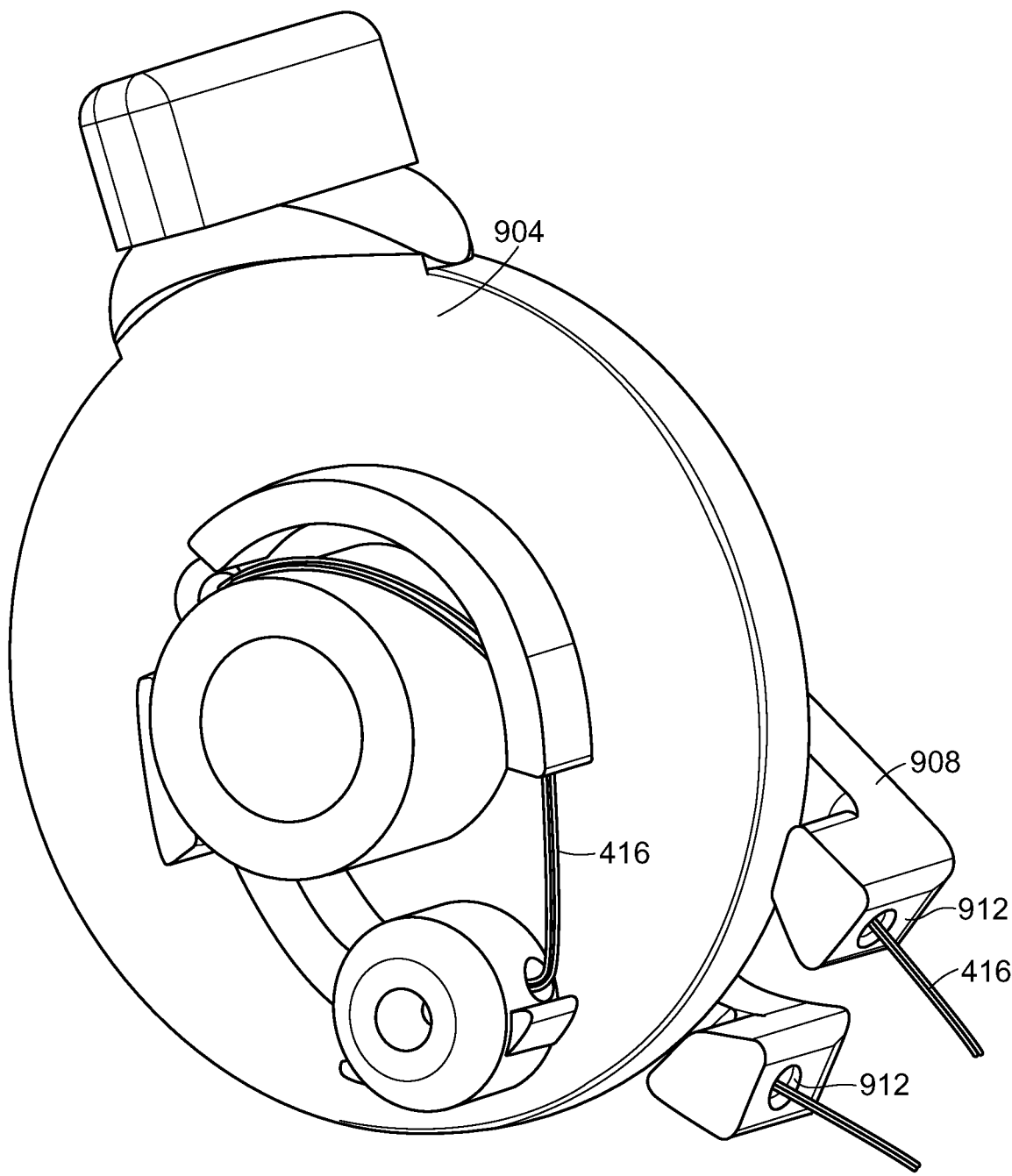

As shown in FIGS. 11-1 and 11-2, the wires 416 feed through one of the openings 912 in the wire cradle 908 on one side and are passed through to the other side and then back through the other one of the openings 912 to close the wire loop.

Once the tip is at the desired location, the flexible actuator pushrod 212 is used to push the repair devices 112 into place. The flexible actuator pushrod 212 may provide tactile feedback and positional control to the user. The flexible portion 220 can be changed to increase or decrease stiffness at the tip.

Figure 12:
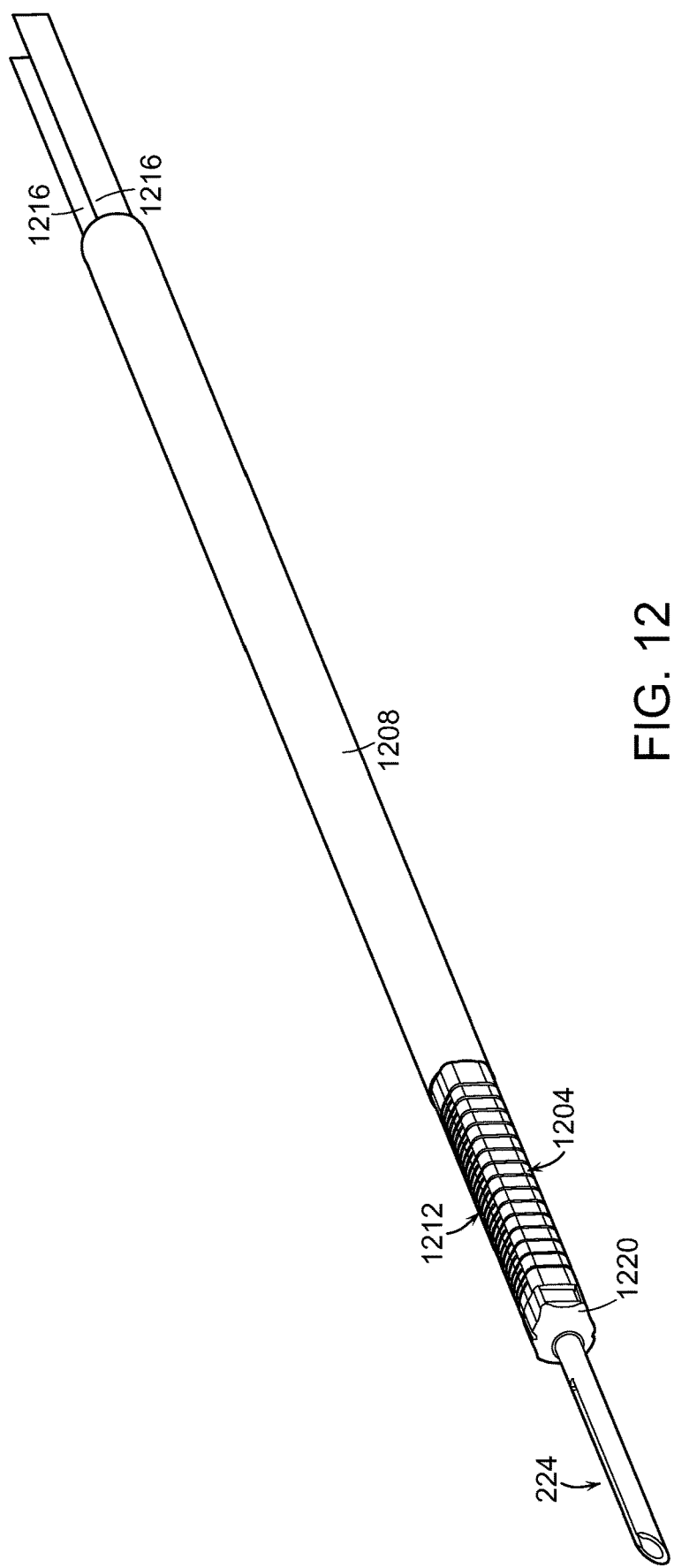
FIG. 12 is a perspective view of a meniscal repair device in accordance with another aspect of the present disclosure.
Figure 13:
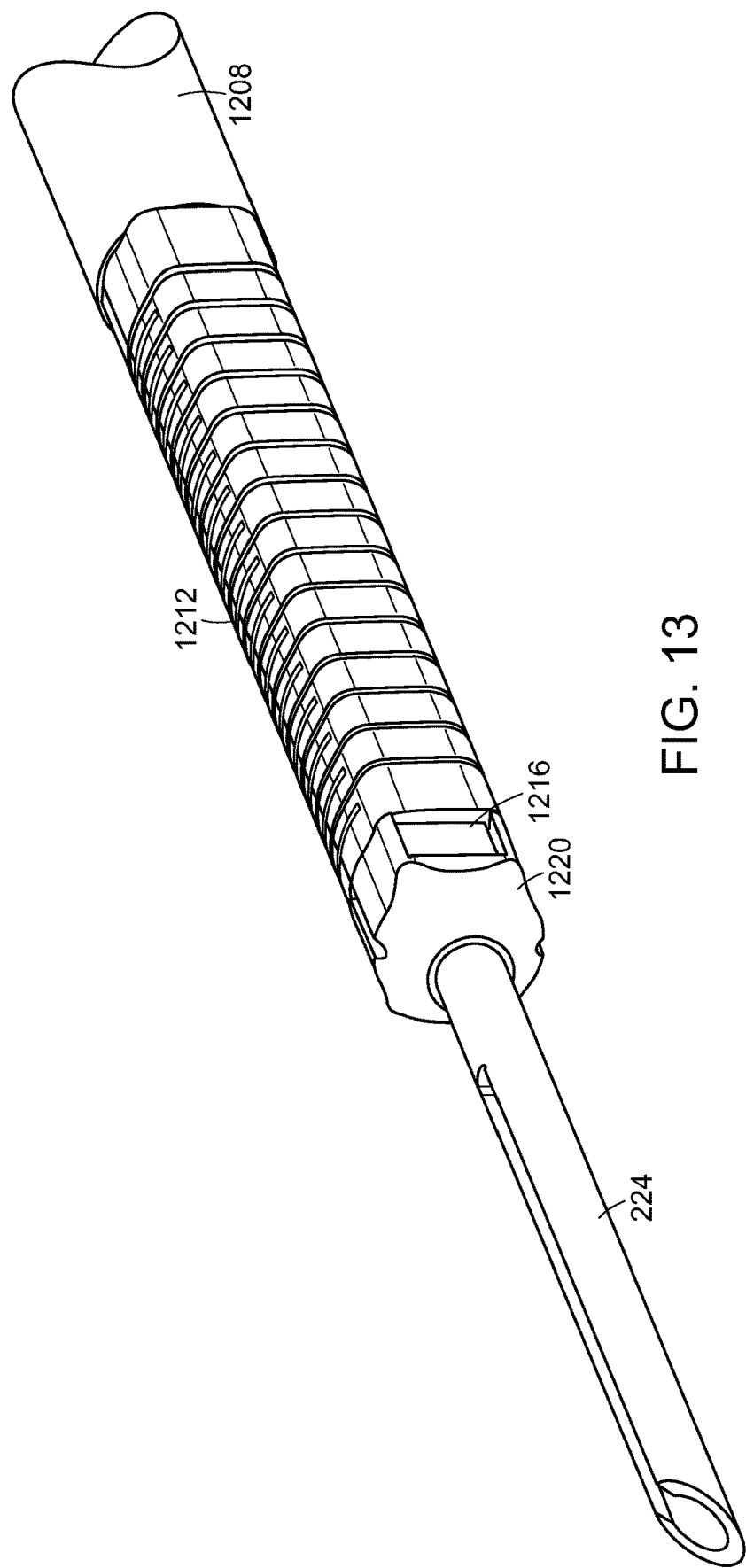
FIG. 13 is a close-up view of a flexible portion of the repair device of FIG. 12.

In an alternate aspect of the present disclosure, a flexible portion 1204 is provided at a distal end of a support tube 1208 intermediate to a needle tip 224, as shown in FIGS. 12 and 13. The flexible portion 1204 includes an articulated tube 1212, for example, a laser-cut flexible tube made of a plastic. Two flexible bands 1216 are provided through the support tube 1208 and terminated in a head portion 1220, as shown. In operation, pulling on one or the other of the bands 1216 will cause the flexible portion 1204 to bend in that direction.

Referring now to FIGS. 14-1 thru 14-3, the articulated tube 1212 includes parallel band guides 1414 through which a respective band 1216 is run and terminated in the head portion 1220.

A length of the articulated tube 1212 can be chosen to determine the radius of curvature as well as the placement, number and thickness of the cuts in the tube 1212.

It is to be understood that the detailed descriptions of the embodiments of the present invention are provided by way of example only and are not intended to limit the scope of the invention. Features and/or steps described with respect to one embodiment may be used with other embodiments and not all embodiments of the invention have all of the features and/or steps shown in a particular figure or described with respect to one of the embodiments. Variations of embodiments described will occur to persons of skill in the art.

Although the present disclosure has been described herein with reference to particular materials and embodiments, the present disclosure is not intended to be limited to the particulars disclosed herein; rather, the present disclosure extends to all functionally equivalent structures, methods and uses, such as are within the scope of the appended claims.

The invention claimed is:

1. A meniscal repair instrument, comprising:
    a flexible shaft having a longitudinal axis;
    an articulating mechanism, disposed about the flexible shaft, comprising:
        a wire formed in a closed loop having a first looped end and a second looped end; and
        a plurality of separately formed, movable members, each of the moveable members having a unitary, annular body disposed about a circumference of the flexible shaft and coupled in series to one another by the wire loop, the annular body defining first and second pairs of through holes, each of two wire strands forming the first looped end extending longitudinally along a first side of the flexible shaft through a different one of the first pair of through holes and each of two wire strands forming the second looped end extending longitudinally along a second side of the flexible shaft through a different one of the second pair of through holes, the articulating mechanism further comprising a terminal movable member; and
    a control mechanism, coupled to the articulating mechanism, configured to move the articulating mechanism through a controlled arc of motion, the control mechanism coupled to the wire loop;

wherein the control mechanism comprises a wire cradle coupled to a first side of a thumbwheel, the wire cradle configured to position at least a portion of the wire loop at an angle with respect to the longitudinal axis;

wherein each of the first and second looped ends extends across a distal face of the terminal movable member and loops back through the terminal movable member to the control mechanism; and wherein the two wire strands forming the first looped end are routed through a first opening in the wire cradle and then around the wire cradle, and then through a second opening in the wire cradle to form the second looped end.

2. The meniscal repair instrument of claim 1, wherein the control mechanism is further configured to push one of the wire strands forming the first looped end and pull another of the wire strands forming the second looped end at a same time.

3. The meniscal repair instrument of claim 1, further comprising:
a holding mechanism, coupled to the articulating mechanism, configured to prevent the wire loop from moving.

4. The meniscal repair instrument of claim 1, further comprising:
a movable member support tube, disposed about the flexible shaft, and coupled to the articulating mechanism, the support tube comprising first and second pairs of conduits,
wherein each of the two wire strands forming the first and second looped ends are disposed, respectively, in a different one of the first and second pairs of conduits.

5. The meniscal repair instrument of claim 4, wherein the first and second pairs of conduits are positioned 180° from one another about a circumference of the flexible shaft.

6. The meniscal repair instrument of claim 1, wherein a coupling portion of one movable member is coupled to a next movable member in the series.

7. The meniscal repair instrument of claim 6, wherein the coupling portion defines a plane in which the controlled arc of motion resides.

8. The meniscal repair instrument of claim 1, wherein the two wire strands forming the first end of the wire loop are further routed from the wire cradle to a second side of the thumbwheel opposite the first side, and back through the thumbwheel to the wire cradle on the first side of the thumbwheel.

9. A meniscal repair instrument, comprising:
a flexible shaft having a longitudinal axis;
a movable member support tube disposed about a portion of the flexible shaft;
an articulating mechanism coupled to the movable member support tube comprising:
a wire formed in a closed loop having a first looped end and a second looped end; and
a plurality of separately formed, movable members, each of the moveable members having a unitary, annular body disposed about a circumference of the flexible shaft and coupled in series to one another by the wire loop, the annular body defining first and second pairs of through holes, each of two wire strands forming the first looped end extending longitudinally along a first side of the flexible shaft through a different one of the first pair of through holes and each of the two wire strands forming the second looped end extending longitudinally along a second side of the flexible shaft through a different one of the second pair of through holes, the articulating mechanism further comprising a terminal movable member;

a control mechanism comprising a wire cradle coupled to the wire loop on a first side of a thumbwheel, the control mechanism configured to push one of the two wire strands forming the first looped end and pull another of the two wire strands forming the second looped end at a same time, the wire cradle configured to position at least a portion of the wire loop at an angle with respect to the longitudinal axis;

an actuator disposed at a proximal end of the moveable member support tube;

a push rod disposed in the flexible shaft and coupled to the actuator; and a needle portion disposed distal to the flexible shaft to define a distal tip of the meniscal repair instrument;

wherein each of the first and second looped ends extends across a distal face of the terminal movable member and loops back through the terminal movable member to the control mechanism; and wherein the two wire strands forming the first looped end are routed through a first opening in the wire cradle and then around the wire cradle, and then through a second opening in the wire cradle to form the second looped end.

10. The meniscal repair instrument of claim 9, further comprising a plurality of implants provided within the movable member support tube.

11. The meniscal repair instrument of claim 10, wherein sutures attached to the implants are confined within the movable member support tube.

12. The meniscal repair instrument of claim 9, further comprising:
a holding mechanism, coupled to the articulating mechanism, configured to prevent the wire loop from moving.

13. The meniscal repair instrument of claim 9, wherein the movable member support tube comprises:
first and second pairs of wire conduits,
wherein each of the two wire strands forming the first and second looped ends are disposed, respectively, in a different one of the first and second pairs of wire conduits.

14. The meniscal repair instrument of claim 13, wherein the first and second pairs of wire conduits are disposed 180° from one another about a circumference of the flexible shaft.

15. The meniscal repair instrument of claim 9, wherein a coupling portion of one movable member is coupled to a next movable member in the series.

16. The meniscal repair instrument of claim 15, wherein the coupling portion defines a plane in which the articulating mechanism operates.

17. The meniscal repair instrument of claim 9, wherein the two wire strands forming the first end of the wire loop are further routed from the wire cradle to a second side of the thumbwheel opposite the first side, and back through the thumbwheel to the wire cradle on the first side of the thumbwheel.

* * * * *